(12) United States Patent
Ford et al.

(10) Patent No.: US 6,511,509 B1
(45) Date of Patent: *Jan. 28, 2003

(54) TEXTURED BONE ALLOGRAFT, METHOD OF MAKING AND USING SAME

(75) Inventors: Louis Ford, Virginia Beach; Lloyd Wolfinbarger, Jr., Norfolk, both of VA (US); Jon C. Serbousek; Laine Mashburn, Jr., both of Winona Lake, IN (US)

(73) Assignee: LifeNet, Virginia Beach, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/073,877

(22) Filed: May 7, 1998

Related U.S. Application Data

(60) Provisional application No. 60/062,823, filed on Oct. 20, 1997.

(51) Int. Cl.⁷ .................................................. A61F 2/28
(52) U.S. Cl. .................................... 623/23.5; 623/23.63
(58) Field of Search ........................ 623/16, 17, 23.63, 623/23.61, 23.5, 16.11

(56) References Cited

U.S. PATENT DOCUMENTS

| | | | |
|---|---|---|---|
| 4,294,753 A | 10/1981 | Urist | 260/112 |
| 4,314,380 A | 2/1982 | Miyata et al. | 3/1.9 |
| 4,472,840 A | 9/1984 | Jeffries | 3/1.9 |
| 4,627,853 A | 12/1986 | Campbell et al. | |
| 4,678,470 A | 7/1987 | Nashef et al. | |
| 4,685,919 A | 8/1987 | Niwa et al. | |
| 4,743,256 A | 5/1988 | Brantigan | |
| 4,820,305 A | 4/1989 | Harms et al. | |
| 4,834,757 A * | 5/1989 | Branhgan | 623/17 |
| 4,877,864 A | 10/1989 | Wang et al. | 530/324 |
| 4,878,915 A | 11/1989 | Brantigan | |
| 4,882,149 A | 11/1989 | Spector | 424/425 |
| 4,950,296 A | 8/1990 | McIntyre | |
| 4,961,740 A | 10/1990 | Ray et al. | 606/69.1 |
| 5,013,649 A | 5/1991 | Wang et al. | 435/69.1 |
| 5,015,247 A | 5/1991 | Michelson | 606/61 |
| 5,026,373 A | 6/1991 | Ray et al. | 606/61 |
| 5,044,104 A | 9/1991 | Hopperdietzel | 40/642 |
| 5,092,893 A | 3/1992 | Smith | |

(List continued on next page.)

FOREIGN PATENT DOCUMENTS

| | | |
|---|---|---|
| EP | 0538183 A1 | 7/1992 |
| FR | 2703580 | 10/1994 |
| WO | WO 93/00432 | 1/1993 |
| WO | WO 94/26892 | 11/1994 |
| WO | WO 94/26893 | 11/1994 |
| WO | WO 97/14378 | 4/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09914 | 3/1999 |
| WO | WO 00/07527 | 2/2000 |
| WO | WO 00/19911 | 4/2000 |
| WO | WO 00/24327 | 5/2000 |

Primary Examiner—Paul J. Hirsch
(74) Attorney, Agent, or Firm—Susanne M Hopkins

(57) ABSTRACT

The present invention is directed to a textured bone allograft for implantation in a patient, having one or more textured bone surfaces, and methods of making and using the textured bone graft. The textured surface preferably includes a plurality of closely spaced discrete, continuous, or a combination thereof, protrusions. The textured bone allograft is useful for repairing bone defects caused by congenital anomaly, disease, or trauma, in a patient, for example, for restoring vertical support of the anterior column. Implantation of the textured bone allograft results in improved graft stability and osteoinductivity, without a decrease in mechanical strength. The textured bone allograft does not shift, extrude or rotate, after implantation.

25 Claims, 3 Drawing Sheets

U.S. PATENT DOCUMENTS

| | | | | |
|---|---|---|---|---|
| 5,106,748 | A | 4/1992 | Wozney et al. | 435/252.3 |
| 5,108,922 | A | 4/1992 | Wang et al. | 435/240.2 |
| 5,116,738 | A | 5/1992 | Wang et al. | 435/69.1 |
| 5,147,402 | A | 9/1992 | Bohler et al. | |
| 5,187,076 | A | 2/1993 | Wozney et al. | 435/69.1 |
| 5,192,327 | A * | 3/1993 | Branhgan | 623/17 |
| 5,275,954 | A | 1/1994 | Wolfinbarger et al. | 436/74 |
| 5,306,303 | A | 4/1994 | Lynch | |
| 5,306,307 | A * | 4/1994 | Senter et al. | 623/17 |
| 5,306,308 | A * | 4/1994 | Gross et al. | 623/17 |
| 5,306,309 | A * | 4/1994 | Wagner et al. | 623/17 |
| 5,366,875 | A | 11/1994 | Wozney et al. | 435/69.1 |
| 5,417,975 | A | 5/1995 | Lussi et al. | 424/435 |
| 5,425,772 | A | 6/1995 | Brantigan | |
| 5,443,514 | A * | 8/1995 | Steffee | 623/17 |
| 5,514,180 | A * | 5/1996 | Heggeness et al. | 623/17 |
| 5,534,030 | A | 7/1996 | Heggeness et al. | |
| 5,556,379 | A | 9/1996 | Navarro et al. | |
| 5,573,771 | A | 11/1996 | Geistlich et al. | 424/422 |
| 5,585,116 | A | 12/1996 | Bonafice et al. | 424/549 |
| 5,609,635 | A * | 3/1997 | Michelson | 623/17 |
| 5,609,637 | A | 3/1997 | Wolfinbarger | 604/49 |
| 5,658,337 | A | 8/1997 | Kohrs et al. | |
| 5,683,464 | A | 11/1997 | Wagner et al. | |
| 5,702,449 | A * | 12/1997 | McKay | 623/17 |
| 5,702,455 | A | 12/1997 | Saggar | |
| 5,709,683 | A | 1/1998 | Bagby | 606/61 |
| 5,716,415 | A | 2/1998 | Steffee | |
| 5,722,977 | A | 3/1998 | Wilhelmy | 606/84 |
| 5,725,579 | A | 3/1998 | Fages et al. | |
| 5,728,159 | A * | 3/1998 | Stroever | 623/17 |
| 5,741,253 | A * | 4/1998 | Michelson | 623/17 |
| 5,766,253 | A | 6/1998 | Brosnahan, III | |
| 5,776,199 | A | 7/1998 | Michelson | |
| 5,785,710 | A | 7/1998 | Michelson | 606/61 |
| 5,797,871 | A | 8/1998 | Wolfinbarger, Jr. | 604/49 |
| 5,814,084 | A | 9/1998 | Grivas et al. | |
| 5,820,581 | A | 10/1998 | Wolfinbarger, Jr. | 604/49 |
| 5,865,845 | A * | 2/1999 | Thalgott | 623/17 |
| 5,865,848 | A | 2/1999 | Baker | |
| 5,888,222 | A | 3/1999 | Coates et al. | |
| 5,888,227 | A * | 3/1999 | Cottle | 623/17 |
| 5,897,593 | A | 4/1999 | Kohrs et al. | |
| 5,972,368 | A | 10/1999 | McKay | 424/423 |
| 5,989,289 | A | 11/1999 | Coates et al. | |
| 6,139,579 | A | 10/2000 | Steffee et al. | |

* cited by examiner

TEXTURED BONE ALLOGRAFT, METHOD OF MAKING AND USING SAME

RELATED APPLICATION

This application claims the benefit of the filing date of Oct. 20, 1997, for related, copending, Provisional U.S. Patent Application Serial No. 60/062,823, hereby incorporated herein in its entirety.

FIELD OF THE INVENTION

The present invention is directed to a textured bone allograft for implantation in a patient, having one or more textured bone surfaces, and methods of making and using the textured bone graft. The textured surface preferably includes a plurality of closely spaced discrete or continuous protrusions. The textured bone allograft is useful for repairing bone defects caused by congenital anomaly, disease, or trauma. The present textured bone allograft promotes the growth of patient bone at an implantation site by promoting osteoinductivity and cellularization, provides added stability and mechanical strength, and does not shift, extrude or rotate, after implantation.

BACKGROUND OF THE INVENTION

In the field of bone grafts, small cut bone grafts and essentially intact bone grafts are implanted at a site in a patient. The success or failure of a bone graft depends on whether the bone graft remains at the implant site, is cellularized, and whether it can withstand the mechanical load. In spinal surgery, there are two primary indications for use of allograft bone: (1) when there is insufficient available autograft bone, and (2) in spinal fusion procedures when a structural element in needed. Typically, bone grafts are affixed at an implant site by fusion. Bone grafts for spinal applications often fail because they are extruded from the implantation site due to shifting, rotation, and slippage of the graft, are not cellularized, or fail mechanically. The present invention solves the problem of graft failure by providing a textured bone allograft which promotes the ingrowth of patient bone at an implantation site by promoting osteoinductivity and cellularization, provides added stability and mechanical strength, and does not shift, extrude or rotate, after implantation.

SUMMARY OF THE INVENTION

The present invention is directed to a textured bone allograft for repairing bone defects caused by congenital anomaly, disease, or trauma, including for example, for restoring vertical support of the anterior column. The present textured bone allografts can be used as structural allografts placed anteriorly in the spine as interbody grafts or as strut grafts spanning multiple segments. Posterior textured bone allografts can be used to supplement autologous bone for spinal fusions in patients who lack sufficient host bone and to avoid significant donor site morbidity. The present inventors have surprisingly discovered that providing a textured bone graft results in improved graft stability and osteoinductivity, without a decrease in mechanical strength.

The present invention is directed to a textured bone allograft having a plurality of closely spaced protrusions.

The present invention is directed to a textured bone allograft having a plurality of closely spaced protrusions where the protrusions are continuous, discrete, or a combination thereof.

The present invention is further directed to a textured bone allograft where the shape of the protrusions include: irregular; pyramidal; cuboidal; cylindrical; conical; and rectangular.

The present invention is directed to a textured bone allograft having a plurality of closely spaced protrusions where the cross-section of a continuous or discrete protrusion may be of any shape including for example: irregular; rectangular; square; oval; round; triangular; trapizoidal; and a regular or irregular curve; or any combination thereof.

The present invention is also directed to a textured bone allograft where the protrusions provided on one or more cut surfaces of the bone allograft are from 0.1 to 5.00 mm in height, preferably 0.3 to 3.0 mm in height, and most preferably 0.5 to 1.5 mm in height.

The present invention is directed to a textured bone allograft having a plurality of discrete protrusions on one or more cut surfaces where the protrusions are sized to be in the range of from about 0.5 to about 10.0 mm in length; 0.5 to about 10.0 mm in width and 0.1 to about 5.0 mm in height.

The present invention is directed to a textured bone allograft having a plurality of discrete protrusions on one or more cut surfaces where the protrusions are sized to be in the range of from about 1.5 to about 5.0 mm in length; 1.5 to about 5.0 mm in width and 0.5 to about 2.0 mm in height.

The present invention is directed to a textured bone allograft including textured fibular wedges; textured humeral wedges; textured femoral wedges; textured tibial wedges; textured fibular trapezoid wedges; textured humeral trapezoid wedges; textured femural trapezoid wedges; textured fibular shafts; textured humeral shafts; and textured femural shafts.

The present invention is also directed to a textured bone allograft having a plurality of protrusions where the protrusions are perpendicular to one or more cut surfaces of the allograft.

The present invention is directed to a textured bone allograft where the plurality of protrusions are located on at least one entire cut surface of the bone allograft.

The present invention is directed to a textured bone allograft where the plurality of protrusions are dimensioned to promote ingrowth of patient bone through increased surface area, at an implantation site.

The present invention is further directed to a textured bone allograft including a plurality of closely spaced protrusions provided on one or more surfaces of the bone allograft.

The present invention is directed to a textured bone allograft where the plurality of continuous protrusions include a plurality of protruding, continuous, concentric rings.

The present invention is further directed to a method of restoring vertical support of the anterior vertebral column by implanting the present textured bone allograft.

The present invention is also directed to a method of making a textured bone allograft by providing the bone allograft with a plurality of closely spaced protrusions on the allograft cut surfaces.

The present invention is further directed to a method for making a textured bone allograft by milling grooves into one or more cut surfaces of the bone allograft to form a plurality of closely spaced protrusions.

BRIEF DESCRIPTION OF THE DRAWINGS

FIG. 1. FIG. 1 illustrates a bone allograft ring implant having a textured upper and lower surface which includes a plurality of closely spaced pyramidal shaped protrusions provided over each entire cut surface of the ring, the protrusions being provided perpendicular to the cut surfaces of the bone allograft.

FIG. 2 illustrates a bone allograft ring implant having a textured upper and lower surface which includes a plurality of closely spaced, continuous linear protrusions having a "▲" shape provided over each entire cut surface of the ring implant, the linear protrusions being provided perpendicular to the cut surfaces of the bone.

DETAILED DESCRIPTION OF THE PREFERRED EMBODIMENTS

I. Definitions

The below definitions serve to provide a clear and consistent understanding of the specification and claims, including the scope to be given such terms.

Bone Allograft. By the term "bone allograft" is intended for the purposes of the present invention, bone including cortical and/or cancellous bone, recovered from a cadaver and processed for implantation into a living patient including for example: fibular wedges; humeral wedges; tibial wedges; fibular trapezoid wedges; humeral trapezoid wedges; femoral trapezoid wedges; fibular shafts and rings; humeral shafts and rings; and femoral shafts and rings; and essentially intact bone grafts including for example proximal and distal femur, femoral head; and small cut bone grafts including for example cancellous cubes, iliac crest wedges, and Cloward dowels.

Figure 2:
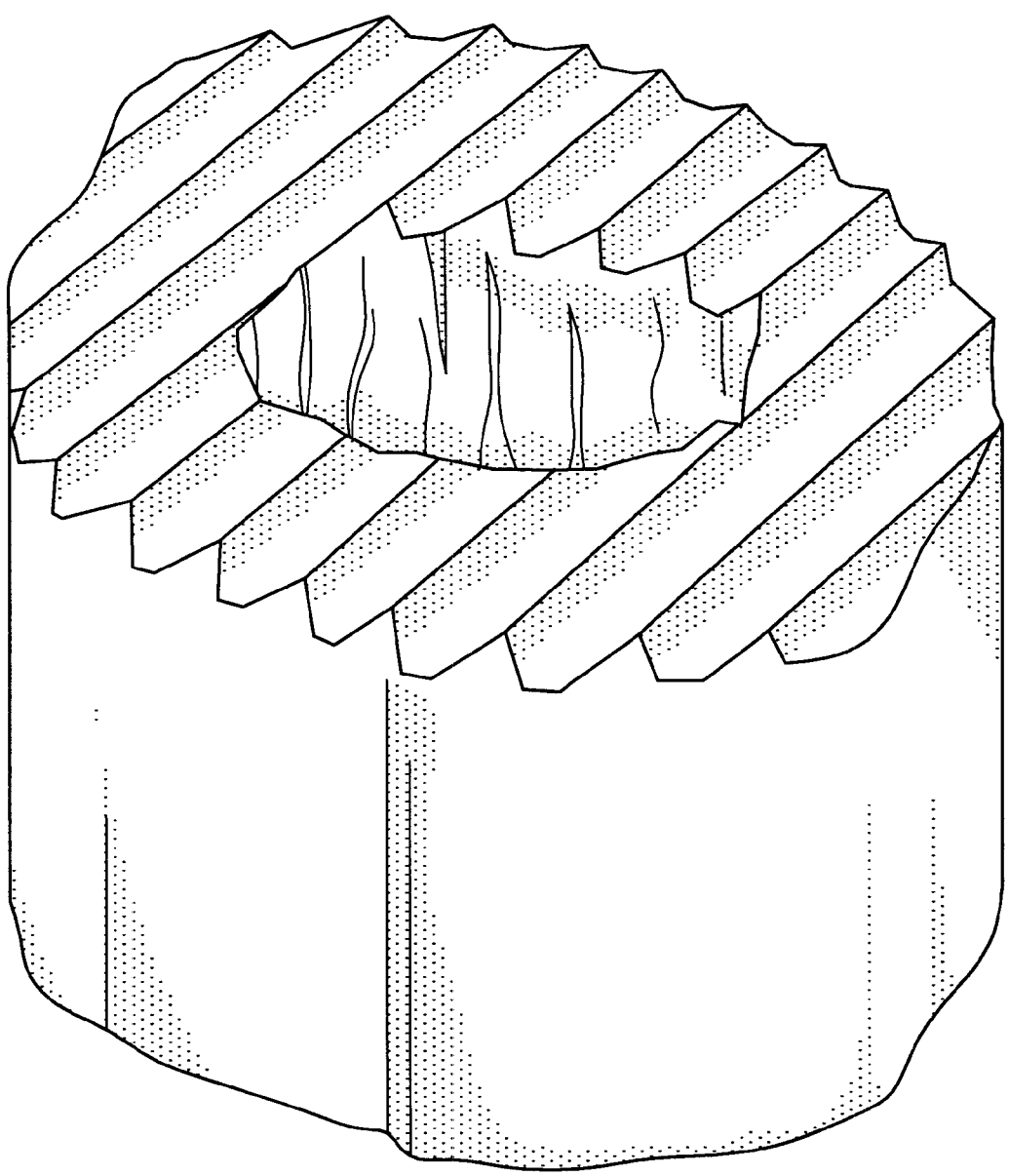
FIG. 2.

Closely Spaced. By the term "closely spaced" is intended for the purposes of the present invention, protrusions (discrete or continuous) which are in close proximity to each other. Preferably the protrusions are spaced no more than 3.0 mm apart (i.e. the distance between the edges of two adjacent protrusions), more preferably no more than 2.0 mm apart, even more preferably no more than 1.5 mm apart, and most preferably about 0.5 mm apart Continuous Protrusion. By the term "continuous protrusion" is intended for the purposes of the present invention, a protrusion whose length continues substantially uninterrupted, including for example a linear or curved protrusion whose length is at least three times greater than its width, preferably at least five times greater, and includes for example a continuous, protruding concentric ring, and a continuous linear protrusion, for example, as illustrated in FIG. 2. Each continuous protrusion may or may not be distinct from another continuous protrusion.

Figure 1A:
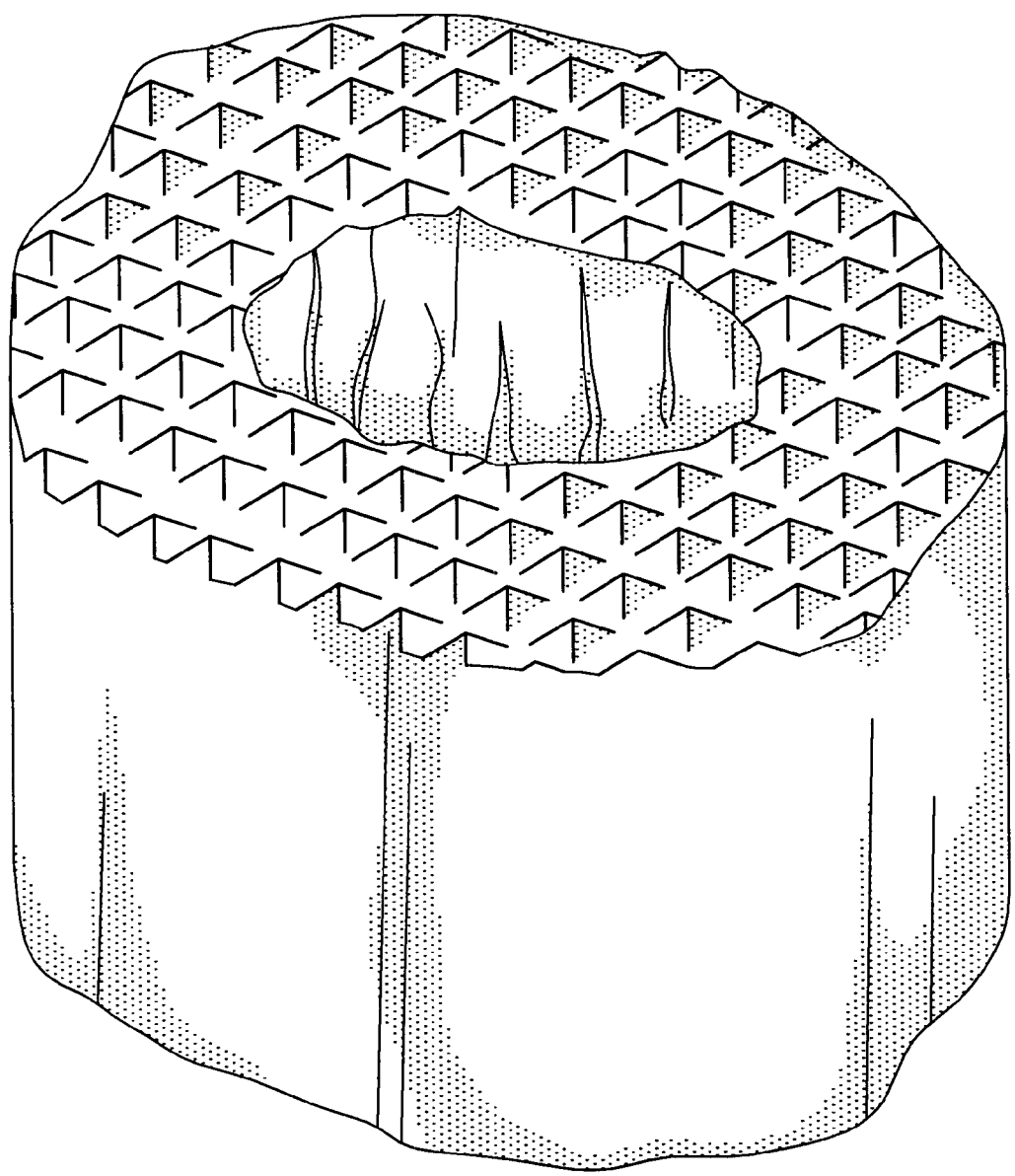
FIG. 1A is a perspective view.
Figure 1B:
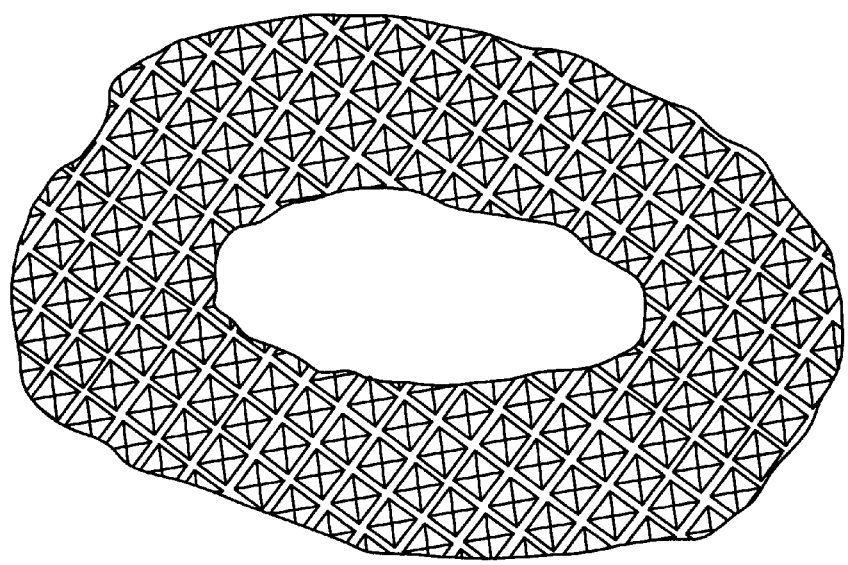
FIG. 1B is a upper planer view.
Figure 1C:
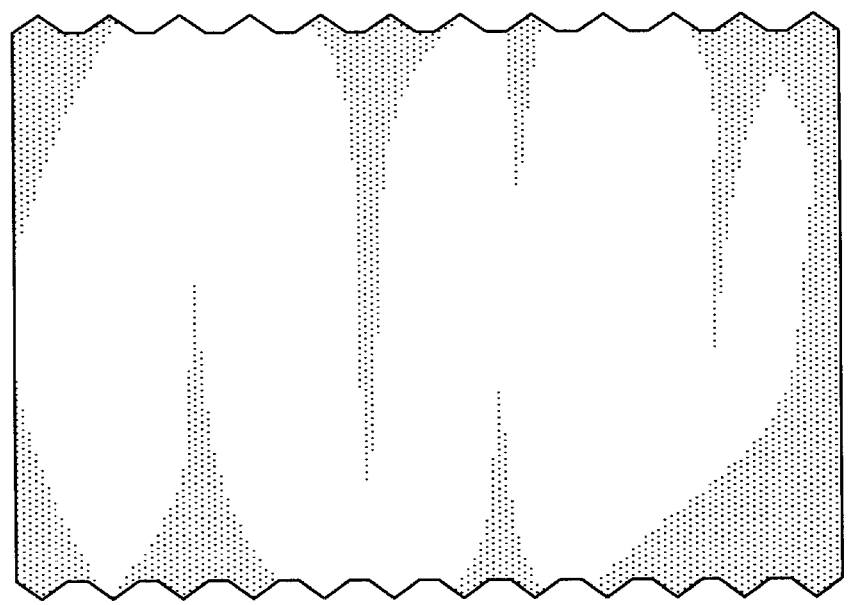
FIG. 1C is a cross-sectional view.

Discrete Protrusion. By the term "discrete protrusion" is intended for the purposes of the present invention, a protrusion which is discontinuous, i.e. which has a distinct length and width, where each discrete protrusion is separate and distinct from every other discrete protrusion, for example, as illustrated in FIG. 1, and includes for example a protrusion whose length is less than three times its width, preferably less than twice its width and more preferably a protrusion whose length is about equal to its width.

Mechanical Strength. By the term "mechanical strength" is intended for the purposes of the present invention, the ability of a bone allograft to withstand mechanical loads at an implant site without failing.

Osteoinductivity. By the term "osteoinductivity" is intended for the purposes of the present invention, the ability to promote bone growth.

Protrusion. By the term "protrusion" is intended for the purposes of the present invention, an irregularity in a surface of a bone allograft having a height of from 0.1 to 5.00 mm, preferably 0.3 to 3.0 mm, and most preferably 0.5 to 1.5 mm. The protrusions can be discrete, continuous, or a combination thereof, and can be of any shape including for example: irregular; pyrimidal; conical; cuboidal; rectangular; and cylindrical; or any combination thereof. Further, a cross-section of a continuous or discrete protrusion maybe of any shape including for example: irregular; rectangular; square; oval; round; triangular; trapizoidal; and a regular or irregular curve; or any combination thereof. The protrusions can be provided on the bone allograft surface in a regular, symmetric pattern including for example a grid-type pattern as illustrated in FIG. 1 or for example, a pattern of concentric rings, or in an irregular pattern.

Stability. By the term "stability" is intended for the purposes of the present invention the ability of the present textured bone allograft to remain at an implantation site without significantly shifting, rotating, or being extruded.

Stress. By the term "stress" is intended for the purposes of the present invention, load per unit cross-sectional area.

Textured Bone Allograft. By the term "textured bone allograft" is intended for the purposes of the present invention, a bone allograft having one or more textured surfaces provided on the surface of a bone allograft where the surface of the bone allograft can be any surface including a natural surface and/or a cut surface. The textured surface preferably includes a plurality of protrusions provided on the surface, the protrusions of a shape including for example, irregular; pyrimidal; conical; cuboidal; rectangular; trapizoidal; curved; and cylindrical; or any combination thereof. The protrusions can be discrete (for example, as illustrated in FIG. 1), or continuous (for example, continuous linear, as illustrated in FIG. 2).

II Description of How to Make and Use a Preferred Embodiment of the Present Textured Bone Allograft The present bone allograft provides a textured surface which increases stability of the graft at an implant site and promotes the ingrowth of patient bone, while providing excellent mechanical strength.

The textured surface includes a plurality of protrusions. The protrusions can be formed over an entire surface of a bone allograft or over a portion of a surface, for example over the entire natural and cut surfaces, over a portion of the natural and/or cut surfaces, or over the entire cut surface. The plurality of protrusions can be formed on the surface in any number of ways well known to those of ordinary skill in the art to which the present invention pertains, including for example mechanical and/or chemical methods, including for example, by forming a series of parallel linear or curved grooves. The bone allograft protrusions illustrated in FIG. 1 are formed by milling a first set of parallel linear groves on the cut surface of the allograft followed by turning the allograft and forming a second set of parallel grooves at an angle to the first series, for example, at a 90° angle. Milling is preferably achieved, by for example: running the graft over a milling tool which includes a plurality of closely spaced blades which can be adjusted to achieve a desired height and width, and then turning the graft at, for example, a 90° angle and again running it over the milling tool to produce the discrete protrusions illustrated in FIG. 1. Milling can also be achieved using for example a routing or dremel tool, a laser, and masking and acid etching.

Other protrusions, for example concentric rings or other curved or irregular, or regular protrusions can be provided by attaching a drill bit having a blade corresponding to the protrusion pattern desired where the blade is appropriately sized to provide a desired protrusion width, length, and height, to a drill and drilling the desired surface of the bone to achieve the desired textured surface. One of ordinary skill in the art can readily design and produce, or select, and employ an appropriate milling tool to achieve a desired textured surface on a bone allograft, without undue experimentation.

Preferably, the protrusions (discrete, continuous, or a combination thereof) present on one or more surfaces of the present allograft are closely spaced, preferably from about 0.0 to 3.0 mm apart, preferably 0.1 to 2.0 mm apart, more preferably about 0.2 to 1.5 mm apart, and most preferably about 0.5 mm apart, (that is, there is preferably a distance of from 0.0 to 3.0 mm between the edges of two adjacent protrusions).

III Procurement and Processing of Allograft Bone Tissue

Allograft tissue is obtained from a cadaver, and processed under strict aseptic conditions in certified clean room operating suites. The bone tissue is preferably processed to remove all soft tissue, including marrow and blood, to produce a cleaned bone graft. Suitable processing methods are well known to those skilled in the art and can be readily selected and employed by those of ordinary skill in the art without undue experimentation. Suitable methods include the methods disclosed in, for example, U.S. Pat. No. 5,556,379. After processing, the cleaned grafts are packaged under sterile conditions and stored for latter processing into the present textured bone allograft, or immediately processed into the present textured bone allograft followed by appropriate packaging. The use of fresh-frozen and/or freeze-dried, bone allografts are preferred.

IV. Textured Bone Allografts

The present textured bone allografts are useful in spinal applications including restoration of anterior column support and can be used from either an anterior or posterior approach. Textured allografts suitable for placement in cervical, thoracic and lumbar interbody fusions preferably include textured wedges including: fibular textured allograft wedges having a diameter of from 8 to 16 mm, preferably 10 to 14 mm, and a height of from 3 to 16 mm, preferably from 5 to 14 mm; humeral textured allograft wedges having a diameter of from 17 to 24 mm, preferably 19 to 22 mm, and a height of from 4 to 16 mm, preferably from 6 to 14 mm; tibial textured allograft wedges having a diameter of from 20 to 30 mm, preferably 23 to 27 mm, and a height of from 4 to 18 mm, preferably from 6 to 16 mm; and femoral textured allograft wedges having a diameter of from 20 to 30 mm, preferably 23 to 27 mm, and a height of from 4 to 18 mm, preferably from 6 to 16 mm.

Textured allografts suitable for use in restoring lordosis in the lumbar spine include textured trapezoid shaped wedges, including for example: fibular textured trapezoid wedges having a diameter of from 8 to 16 mm, preferably 10 to 14 mm, and a height of from 3 mm×6 mm to 13 mm×16 mm, preferably from 5 mm×8 mm to 11 mm×14 mm; humeral textured trapezoid wedges having a diameter of from 17 to 24 mm, preferably 19 to 22 mm, and a height of from 4 mm×12 mm to 19 mm×22 mm, preferably from 11 mm×14 mm to 17 mm×20 mm; and femoral textured trapezoid wedges having a diameter of from 21 to 29 mm, preferably 23 to 27 mm, and a height of from 4 mm ×12 mm to 19 mm×22 mm, preferably from 11 mm×14 mm to 17 mm×20 mm.

Textured allografts suitable for addressing large column defects include textured allograft shafts, including for example: fibular textured shafts having a diameter of from 8 to 16 mm, preferably 10 to 14 mm, and a height of from 10 to 60 mm, preferably from 20 to 50 mm; humeral textured shafts having a diameter of from 17 to 24 mm, preferably 19 to 22 mm, and a height of from 10 to 60 mm, preferably from 20 to 50 mm; and femoral textured shafts having a diameter of from 21 to 29 mm, preferably 23 to 27 mm, and a height of from 30 to 80 mm, preferably from 40 to 70 mm.

The present textured bone allografts are preferably textured with a plurality of closely spaced protrusions over their entire opposing cut surfaces. Other suitable grafts for cervical fusion include textured iliac crest bone allografts.

V. Surgical Implantation and Indications

The present textured bone allograft is useful for implantation in patients suffering from defects caused by congenital anomaly, disease, or trauma, including for example, spine fractures; deformity, e.g. kyphotic deformities, e.g. posttraumatic kyphosis; postlaminectomy kyphosis, junctional kyphosis, and Scheuermann's kyphosis; scoliosis, e.g. neuromuscular scoliosis, adult scoliosis, paralytic scoliosis, congenital and syndromic scoliosis; and cervical neck pain. Surgical methods for correcting degenerative conditions, for example in the lumbar spine, include decompression (excision of disc material, hypertrophied bone, or ligament along with fusion, or fusion alone.

An anterior or posterior surgical approach can be used. The choice of approach is dictated by the site of primary pathology. Pathology that involves vertebral bodies is best approached anteriorly through the thorax, abdomen or flank. Pathology involving posterior elements are best approached posteriorly for example, through a vertical midline approach or posterior lateral muscle spinning approach.

Those of ordinary skill in the art to which the present invention pertain, e.g. an orthopaedic surgeon, a spinal surgeon, etc., can readily select and employ a particular textured bone allograft, without undue experimentation. Factors to be considered in such selection and employment include: the type of allograft bone, its anatomic site of fusion, and the age of the patient. An ideal graft, for example for use in lumbar interbody fusion, should be: osteoinductive, non-immunogenic, provide immediate mechanical stability, and be appropriately sized and shaped for the particular application/patient. Indications, diagnostic criteria, graft selection and surgical technique, are factors that can be readily selected, optimized and employed by those of ordinary skill in the art without undue experimentation, and are discussed in: Master Techniques in Orthopaedic Surgery, *The Spine*, edited by Bradford, David S., Lippincott-Raven, ISBN 0-7817-0033-7, Philadelphia, Pa., (1997), hereby incorporated herein by reference in its entirety.

It is to be understood, however, that the scope of the present invention is not to be limited to the specific embodiments described above. The invention may be practiced other than as particularly described and still be within the scope of the accompanying claims.

We claim:

1. A textured bone allograft comprising: a plurality of closely spaced protrusions, each protrusion comprising a triangular shaped cross-section.

2. The textured bone allograft of claim 1, said plurality of closely spaced protrusions comprise a plurality of closely spaced discrete protrusions or a plurality of closely spaced continuous protrusions.

3. The textured bone allograft of claim 2, said plurality of closely spaced protrusions are provided on one or more surfaces of said bone allograft.

4. The textured bone allograft of claim 2, said plurality of closely spaced protrusions comprise a plurality of closely spaced discrete protrusions.

5. The textured bone allograft of claim 2, said closely spaced protrusions comprise closely spaced continuous protrusions.

6. The textured bone allograft of claim 4, said closely spaced discrete protrusions comprising a plurality of closely spaced discrete pyramidal protrusions.

7. The textured bone allograft of claim 4, said closely spaced discrete protrusions comprising a plurality of closely spaced discrete conical protrusions.

8. The textured bone allograft of claim 5, said closely spaced continuous protrusions are linear.

9. The textured bone allograft of claim 5, said closely spaced continuous protrusions are nonlinear.

10. The textured bone allograft of any one of claims 1, 2, 4, or 5, said plurality of closely spaced protrusions are spaced from about 0.0 mm to about 3.0 mm apart.

11. The textured bone allograft of claim 10, said plurality of closely spaced protrusions are spaced from about 0.1 mm to about 2.0 mm apart.

12. The textured bone allograft of claim 11, said plurality of closely spaced protrusions are spaced about 0.5 mm apart.

13. The textured bone allograft of any one of claims 1, 2, 4, or 5, said plurality of closely spaced protrusions are from about 0.1 mm to about 5.0 mm in height.

14. The textured bone allograft of claim 13, said plurality of closely spaced protrusions are from about 0.3 mm to about 3.0 mm in height.

15. The textured bone allograft of claim 14 said plurality of closely spaced protrusions are from about 0.5 mm to about 2.0 mm in height.

16. The textured bone allograft of any one of claims 1, 2, 4, or 5, said bone allograft is selected from the group consisting of: a fibular wedge; a humeral wedge; a tibial wedge; a fibular trapezoid wedge; a humeral trapezoid wedge; a femoral wedge; a femoral trapezoid wedge; a fibular ring; a fibular shaft; a humeral ring; a humeral shaft; a femoral ring; a femoral shaft; a cancellous cube, a Cloward dowel; an iliac crest wedge; a proximal femur; a distal femur; and a femoral head.

17. The textured bone allograft of claim 3, said plurality of protrusions are provided on at least one entire cut surface of said bone allograft.

18. The textured bone allograft of claim 4, said plurality of closely spaced discrete protrusions are sized to be in a range of from about 0.5 mm to about 10.0 mm in length, 0.5 mm to about 10.0 mm in width, and 0.1 to about 5.0 mm in height.

19. The textured bone allograft of claim 18, said plurality of closely spaced discrete protrusions are sized to be in a range of from about 1.5 mm to about 5.0 mm in length, 1.5 mm to about 5.0 mm in width, and 0.5 to about 2.0 mm in height.

20. The textured bone allograft of claim 5, said plurality of closely spaced continuous protrusions are sized to be in a range of from greater than or equal to about 1.5 mm in length, 0.5 mm to about 10.0 mm in width, and 0.1 to about 5.0 mm in height.

21. The textured bone allograft of claim 20, said plurality of closely spaced continuous protrusions are sized to be in a range of from greater than or equal to about 4.5 mm in length, 1.5 mm to about 5.0 mm in width, and 0.5 to about 2.0 mm in height.

22. The textured bone allograft of any one of claims 1, 2, 4, or 5, said plurality of protrusions are provided perpendicular to a surface of said bone allograft.

23. A method for restoring vertical support of the anterior column, comprising: implanting a textured bone allograft comprising a plurality of closely spaced protrusions, each protrusion comprising a triangular shaped cross-section, said plurality of closely spaced discrete protrusions provided on one or more surfaces of said bone allograft, at a site in a patient.

24. A method of making a textured bone allograft, comprising: providing said bone allograft with a plurality of closely spaced protrusions each protrusion comprising a triangular shaped cross-section, on one or more surfaces of said bone allograft.

25. The method of any one of claims 23 or 24, said closely spaced protrusions comprise discrete protrusions or continuous protrusions.

* * * * *

(12) EX PARTE REEXAMINATION CERTIFICATE (10302nd)

United States Patent
Ford et al.

(10) Number: US 6,511,509 C1
(45) Certificate Issued: Sep. 30, 2014

(54) TEXTURED BONE ALLOGRAFT, METHOD OF MAKING AND USING SAME

(75) Inventors: Louis Ford, Virginia Beach, VA (US); Lloyd Wolfinbarger, Jr., Norfolk, VA (US); Jon C. Serbousek, Winona Lake, IN (US); Laine Mashburn, Jr., Winona Lake, IN (US)

(73) Assignee: Depuy Motech Acromed, Inc., Cleveland, OH (US)

Reexamination Request:
No. 90/009,348, Dec. 3, 2008

Reexamination Certificate for:
Patent No.: 6,511,509
Issued: Jan. 28, 2003
Appl. No.: 09/073,877
Filed: May 7, 1998

Related U.S. Application Data

(60) Provisional application No. 60/062,823, filed on Oct. 20, 1997.

(51) Int. Cl.
*A61F 2/28* (2006.01)
*A61F 2/44* (2006.01)
*A61F 2/00* (2006.01)
*A61F 2/30* (2006.01)
*A61F 2/46* (2006.01)

(52) U.S. Cl.
USPC .................................. 623/23.5; 623/23.63

(58) Field of Classification Search
USPC ............ 623/16.11, 17.11, 17.16, 23.5, 23.61, 623/23.63; 606/249
See application file for complete search history.

(56) References Cited

To view the complete listing of prior art documents cited during the proceeding for Reexamination Control Number 90/009,348, please refer to the USPTO's public Patent Application Information Retrieval (PAIR) system under the Display References tab.

*Primary Examiner* — David O. Reip

(57) ABSTRACT

The present invention is directed to a textured bone allograft for implantation in a patient, having one or more textured bone surfaces, and methods of making and using the textured bone graft. The textured surface preferably includes a plurality of closely spaced discrete, continuous, or a combination thereof, protrusions. The textured bone allograft is useful for repairing bone defects caused by congenital anomaly, disease, or trauma, in a patient, for example, for restoring vertical support of the anterior column. Implantation of the textured bone allograft results in improved graft stability and osteoinductivity, without a decrease in mechanical strength. The textured bone allograft does not shift, extrude or rotate, after implantation.

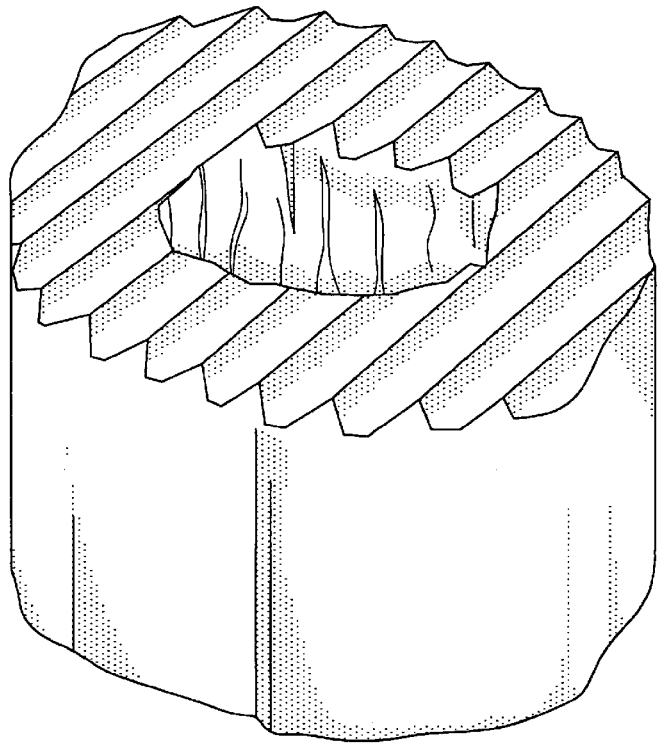

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-8 and 11-25 are cancelled.

Claims 9 and 10 are determined to be patentable as amended.

New claims 26-30 are added and determined to be patentable.

9. The textured bone allograft of claim [5] *10*, said closely spaced continuous protrusions are nonlinear.

10. [The textured bone allograft of any one of claim 1, 2, 4, or 5, said plurality of closely spaced protrusions] *A textured bone allograft comprising:*
   *an allograft ring having:*
      *an upper cut surface,*
      *a lower cut surface, and*
      *a plurality of closely spaced continuous protrusions located on each of the upper and lower cut surfaces, each continuous protrusion having a triangular shaped cross-section;*
   *wherein the plurality of closely spaced protrusions are* are spaced from about 0.0 mm to about 3.0 mm apart*; and*
   *wherein the closely spaced continuous protrusions are provided over each entire cut surface of the ring.*

26. *The textured bone allograft of claim 10, wherein said closely spaced continuous protrusions are linear.*

27. *The textured bone allograft of claim 10, wherein said plurality of closely spaced protrusions are spaced from about 0.1 mm to about 2.0 mm apart.*

28. *The textured bone allograft of claim 27, said plurality of closely spaced protrusions are spaced about 0.5 mm apart.*

29. *The textured bone allograft of claim 10, wherein said plurality of closely spaced continuous protrusions are sized to be in a range of from greater than or equal to about 1.5 mm in length, 0.5 mm to about 10.0 mm in width, and 0.1 to about 5.0 mm in height.*

30. *The textured allograft of claim 29, wherein said plurality of closely spaced continuous protrusions are sized to be in a range of from greater than or equal to about 4.5 mm in length, 1.5 mm to about 5.0 mm in width, and 0.5 to about 2.0 mm in height.*

* * * * *